US00PP17068P2

(12) United States Plant Patent
Dümmen

(10) Patent No.: US PP17,068 P2
(45) Date of Patent: Aug. 29, 2006

(54) POINSETTIA PLANT NAMED 'DUEPREMPICA'

(50) Latin Name: *Euphorbia pulcherrima*
Varietal Denomination: Dueprempica

(75) Inventor: Marga Dümmen, Rheinberg (DE)

(73) Assignee: Dummen Jungpflanzen GbR, Rheinberg (DE)

( * ) Notice: Subject to any disclaimer, the term of this patent is extended or adjusted under 35 U.S.C. 154(b) by 0 days.

(21) Appl. No.: 11/174,972

(22) Filed: Jul. 5, 2005

(51) Int. Cl.
*A01H 5/00* (2006.01)

(52) U.S. Cl. ..... Plt./303
(58) Field of Classification Search ..... Plt./303
See application file for complete search history.

*Primary Examiner*—Kent Bell
(74) *Attorney, Agent, or Firm*—C. A. Whealy

(57) ABSTRACT

A new and distinct cultivar of Poinsettia plant named 'Dueprempica', characterized by its inflorescences with red and pale yellow-colored flower bracts; uniform and rounded plant habit; freely branching habit; early flowering habit; and excellent post-production longevity.

1 Drawing Sheet

Botanical denomination: *Euphorbia pulcherrima* Willd.
Cultivar designation: 'Dueprempica'.

CROSS-REFERENCE TO RELATED APPLICATIONS

Poinsettia Plant Named 'Duepremimapri'; Marga Dümmen, disclosed in U.S. Plant patent application Ser. No. 11/174,980; Poinsettia Plant Named 'Duepremmar'; Marga Dümmen, disclosed in U.S. Plant patent application Ser. No. 11/174,967; and Poinsettia Plant Named 'Duepremmiro'; Marga Dümmen, disclosed in U.S. Plant patent application Ser. No. 11/174,972;

BACKGROUND OF THE INVENTION

The present Invention relates to a new and distinct cultivar of Poinsettia plant, botanically known as *Euphorbia pulcherrima* Willd., and hereinafter referred to by the name 'Dueprempica'.

The new Poinsettia is a product of a planned breeding program conducted by the Inventor in Rheinberg, Germany. The objective of the breeding program is to create new Poinsettia cultivars with uniform plant habit and attractive flower bract coloration.

The new Poinsettia is a naturally-occurring whole plant mutation of a proprietary selection of *Euphorbia pulcherrima* Willd. identified as code number E-16-18, not patented. The cultivar Dueprempica was discovered and selected by the Inventor as a flowering plant within a population of plants of the parent selection in a controlled environment in Rheinberg, Germany in December, 2003. The selection of this plant was based on its attractive flower bract coloration.

Asexual reproduction of the new Poinsettia by vegetative terminal cuttings taken at Rheinberg, Germany since December, 2003, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Dueprempica'. These characteristics in combination distinguish 'Dueprempica' as a new and distinct cultivar:

1. Inflorescences with red and pale yellow-colored flower bracts.
2. Uniform and rounded plant habit.
3. Freely branching habit.
4. Early flowering habit; response time, about seven weeks.
5. Excellent post-production longevity.

Plants of the new Poinsettia differ primarily from plants of the parent selection in flower bract coloration as plants of the parent selection have red-colored flower bracts.

Plants of the new Poinsettia can be compared to plants of the Poinsettia cultivar Duepremimapri, disclosed in U.S. Plant patent application Ser. No. 11/174,980; the Poinsettia cultivar Duepremmar, disclosed in U.S. Plant patent application Ser. No. 11/174,967; and the Poinsettia cultivar Duepremmiro, disclosed in U.S. Plant patent application Ser. No. 11/174,972. Plants of the new Poinsettia differ primarily from plants of the cultivars Duepremimapri, Duepremmar and Duepremmiro in flower bract coloration.

Plants of the new Poinsettia can be compared to plants of the cultivar Duepre, disclosed in U.S. Plant Pat. No. 13,644. In side-by-side comparisons conducted in Rheinberg, Germany, plants of the new Poinsettia differed from plants of the cultivar Duepre in the following characteristics:

1. Plants of the new Poinsettia had smaller leaves than plants of the cultivar Duepre.
2. Plants of the new Poinsettia and the cultivar Duepre differed in flower bract coloration as plants of the cultivar Duepre had red-colored flower bracts.

BRIEF DESCRIPTION OF THE PHOTOGRAPH

The accompanying colored photograph illustrates the overall appearance of the new Poinsettia, showing the colors as true as it is reasonably possible to obtain in colored reproductions of this type. Colors in the photograph differ slightly from the color values cited in the detailed botanical description which accurately describe the colors of the new Poinsettia. The photograph comprises a side perspective view of a single flowering plant of 'Dueprempica' grown in a container.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype.

The aforementioned photograph, following observations and averaged measurements describe plants grown in Rheinberg, Germany during the winter under commercial practice in a glass-covered greenhouse with day and night temperatures about 22° C. and light levels about 4,500 lux. Single plants were grown in 13-cm containers and pinched once about five weeks after planting. Plants were flowered under natural season short day/long night conditions. Plants were about 16 weeks from unrooted cuttings when the photograph and the detailed botanical description were taken.

In the following description, color references are made to The Royal Horticultural Society Colour Chart, 1995 Edition, except where general terms of ordinary dictionary significance are used.

Botanical classification: *Euphorbia pulcherrima* Willd. cultivar Dueprempica.

Parentage: Naturally-occurring whole plant mutation of a proprietary selection of *Euphorbia pulcherrima* Willd. identified as code number E-16-18, not patented.

Propagation:

*Type cutting.*—Vegetative terminal cuttings.

*Time to initiate roots.*—Summer: About 9 days at 22° C. Winter: About 13 days at 22° C.

*Time to develop roots.*—Summer: About three weeks at 22° C. Winter: About four weeks at 22° C.

*Root description.*—Fibrous, fleshy; white in color.

*Rooting habit.*—Freely branching, dense.

Plant description:

*Plant form.*—Inverted triangle, top of plant rounded.

*Growth habit.*—Upright and uniform plant habit; moderately vigorous.

*Plant height.*—About 21 cm.

*Plant diameter or spread.*—About 31 cm.

*Lateral branch description.*—Quantity per plant: Freely branching habit; about six lateral branches develop after pinching. Length: About 17 cm. Diameter: About 6 mm. Internode length: About 1.4 cm. Color: 137C.

*Foliage description.*—Arrangement: Alternate, single. Length: About 10.5 cm. Width: About 6.5 cm. Shape: Ovate. Apex: Apiculate. Base: Obtuse. Margin: Entire with irregular lobing. Venation pattern: Pinnate. Texture, upper and lower surfaces: Glabrous, smooth. Surface: Mostly flat. Color: Developing foliage, upper surface: 141B. Developing foliage, lower surface: 138A. Fully expanded foliage, upper surface: 139A. Fully expanded foliage, lower surface: 138A. Venation, upper surface: 146C. Venation, lower surface: 144B. Petiole: Length: About 3.8 cm. Diameter: About 2 mm. Texture, upper and lower surfaces: Glabrous, smooth. Color, upper and lower surfaces: 59A.

Inflorescence description:

*Inflorescence type and habit.*—Inflorescences are compound corymbs of cyathia with colored flower bracts subtending the cyathia. Inflorescences are not fragrant. Inflorescences persistent.

*Natural flowering season.*—Autumn/winter in Northern Hemisphere. Flower initiation and development is induced under long nyctoperiod conditions. Early flowering habit, response time, about seven weeks after start of long nyctoperiod conditions.

*Post-production longevity.*—Plants of the new Poinsettia maintain good substance and bract color for about eight weeks under interior conditions and about twelve weeks under greenhouse conditions.

*Quantity of inflorescences per plant.*—One per lateral branch, about six.

*Inflorescence size.*—Diameter: About 20 cm. Height (depth): About 2.5 cm.

*Flower bracts.*—Quantity of flower bracts per inflorescence: About 17. Length, largest bracts: About 8.8 cm. Width, largest bracts: About 5.5 cm. Shape: Mostly ovate. Apex: Apiculate. Base: Obtuse. Margin: Entire with irregular lobing. Texture, upper and lower surfaces: Glabrous, velvety. Surface: Smooth. Orientation: Mostly horizontal. Color: Developing bracts, upper and lower surfaces: Ground color, 3C densely overlain with random speckles, 46A. Fully expanded bracts, upper and lower surfaces: Ground color, 3C overlain with random speckles, 45A. Venation, upper and lower surfaces: Same as lamina. Flower bract petiole: Length: About 1.6 cm. Diameter: About 2 mm. Texture, upper and lower surfaces: Glabrous, smooth. Color, upper and lower surfaces: 141B.

*Cyathia.*—Quantity of cyathia per corymb: About eight. Diameter of cyathia cluster: About 2.5 cm. Length: About 8 mm. Diameter: About 6 mm. Shape: Ovoid. Color, immature: 144B. Color, mature: 144A.

*Peduncle.*—Length: About 3 mm. Diameter: About 2.5 mm. Strength: Strong. Aspect: Curved. Color: 144B.

*Stamens.*—Quantity of stamens and staminodes per cyathium: About 40. Anther shape: Oval. Anther length: About 0.7 mm. Anther color: 31A. Amount of pollen: Abundant. Pollen color: 14B.

*Pistils.*—Quantity of pistils per cyathium: One. Pistil length: About 1.1 cm. Style length: About 4 mm. Style color: 53B. Stigma color: 53A. Ovary color: 144B.

*Nectaries.*—Quantity of nectaries per cyathium: One. Length: About 5 mm. Color: 14A to 14B.

Disease/pest resistance: Resistance to pathogens and pests common to Poinsettias has not been observed on plants grown under commercial conditions.

Temperature tolerance: Plants of the new Poinsettia have been observed to tolerate temperatures from 12 to 40° C.

It is claimed:

1. A new and distinct cultivar of Poinsettia plant named 'Dueprempica', as illustrated and described.

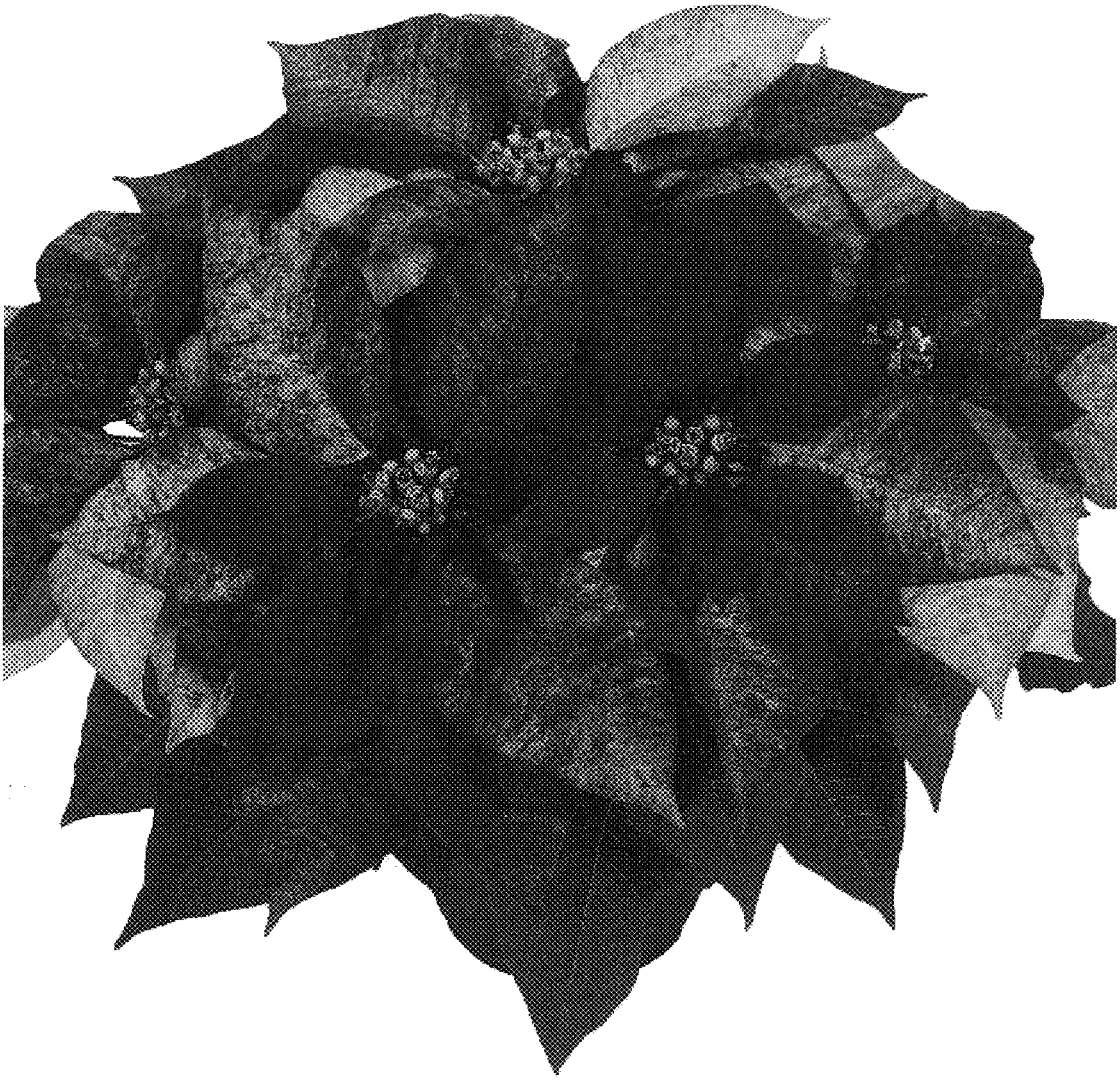

* * * * *